(12) United States Patent
Scharlack et al.

(10) Patent No.: US 7,551,760 B2
(45) Date of Patent: *Jun. 23, 2009

(54) REGISTRATION OF 3D IMAGING OF 3D OBJECTS

(75) Inventors: Ronald S. Scharlack, Brookline, MA (US); Bethany F. Grant, Scituate, MA (US); Alexander Yarmarkovich, Swampscott, MA (US)

(73) Assignee: Astra Tech Inc., Waltham, MA (US)

( * ) Notice: Subject to any disclaimer, the term of this patent is extended or adjusted under 35 U.S.C. 154(b) by 15 days.

This patent is subject to a terminal disclaimer.

(21) Appl. No.: 11/803,153

(22) Filed: May 11, 2007

(65) Prior Publication Data

US 2008/0002869 A1 Jan. 3, 2008

Related U.S. Application Data

(63) Continuation of application No. 11/184,396, filed on Jul. 18, 2005, which is a continuation-in-part of application No. 10/154,717, filed on May 24, 2002, now Pat. No. 6,925,198.

(60) Provisional application No. 60/293,299, filed on May 24, 2001.

(51) Int. Cl.
*G06K 9/00* (2006.01)

(52) U.S. Cl. ........................ 382/128; 382/154

(58) Field of Classification Search ................ 382/128, 382/154

See application file for complete search history.

(56) References Cited

U.S. PATENT DOCUMENTS

| | | | |
|---|---|---|---|
| 4,859,181 A | 8/1989 | Neumeyer | |
| 5,237,998 A | 8/1993 | Duret et al. | |
| 5,338,198 A | 8/1994 | Wu et al. | |
| 5,598,515 A | 1/1997 | Shashua | |
| 5,642,293 A | 6/1997 | Manthey et al. | |
| 5,851,115 A | 12/1998 | Carlsson et al. | |
| 5,857,853 A | 1/1999 | van Nifterick et al. | |
| 6,108,497 A | 8/2000 | Nakayama et al. | |
| 6,152,731 A | 11/2000 | Jordan et al. | |
| 6,318,994 B1 | 11/2001 | Chishti et al. | |
| 6,402,707 B1 | 6/2002 | Ernst | |
| 6,405,071 B1 | 6/2002 | Analoui | |
| 6,505,148 B1 | 1/2003 | Mack et al. | |

(Continued)

FOREIGN PATENT DOCUMENTS

WO    WO 02/102270    12/2002

(Continued)

*Primary Examiner*—Tom Y Lu
(74) *Attorney, Agent, or Firm*—Finnegan, Henderson, Farabow, Garrett & Dunner (57) ABSTRACT

A three-dimensional-based modeling method and system designed for dentistry and related medical (and appropriate non-medical) applications. Data capture means produces a point cloud representing the three-dimensional surface of an object (e.g., dental arch). Three-dimensional recognition objects are provided, particularly within those areas in the image field that have low image definition, and particularly in such of these areas that appear in overlapping portions of at least two images, to provide the three-dimensional image processing software with position, angulation, and orientation information sufficient to enable highly accurate combining (or "stitching") of adjoining and overlapping images. Alignment, and creation of aligned related objects or models thereof, such as maxillar and mandibular arches, is facilitated.

19 Claims, 4 Drawing Sheets

U.S. PATENT DOCUMENTS

| | | |
|---|---|---|
| 6,558,162 B1 | 5/2003 | Porter et al. |
| 6,579,095 B2 | 6/2003 | Marshall et al. |
| 6,925,198 B2 | 8/2005 | Scharlack et al. |
| 7,133,042 B2 | 11/2006 | Anh et al. |
| 7,362,890 B2 | 4/2008 | Scharlack et al. |
| 2002/0028418 A1 | 3/2002 | Farag et al. |
| 2002/0081554 A1 | 6/2002 | Marshall et al. |
| 2003/0012423 A1 | 1/2003 | Boland et al. |
| 2005/0123180 A1 | 6/2005 | Luo et al. |
| 2006/0127858 A1 | 6/2006 | Wen |

FOREIGN PATENT DOCUMENTS

| | | |
|---|---|---|
| WO | WO 03/100729 | 12/2003 |

REGISTRATION OF 3D IMAGING OF 3D OBJECTS

RELATED APPLICATIONS

This application is a continuation of U.S. patent application Ser. No. 11/184,396 filed Jul. 18, 2005, which is a continuation-in-part of U.S. patent application Ser. No. 10/154,717 filed May 24, 2002, which claims priority from Provisional Application Ser. No. 60/293,299 filed May 24, 2001.

BACKGROUND OF INVENTION

Field of Invention

The invention relates to a method and system for determining the relative location of objects and features in a plurality of scanned images. The invention is particularly directed to medical and dental applications including those that require surgical and prosthetic devices to be designed and manufactured to precise dimensions dictated by the anatomy of individual patients, and still more particularly directed to the problem of registering, as precisely as possible, digitized 3-D scans of the mandible and maxilla of a patient or, equivalently, casts or impressions of same.

Many surgical procedures concern the temporary or permanent insertion, into the soft or bony tissue of a patient, of prosthetic and other artificial devices that are required to fit the anatomy of the patient to a very high degree of precision and accuracy. One such application concerns implant dentistry, in the course of which one or more (usually metallic) implant anchors are surgically placed within the jawbone of a patient, to receive and support prosthetic components designed to simulate and replace one or more natural teeth lost by the patient. It is well known that, to be wholly successful, implant procedures must adhere to very strict placement, orientation and sizing requirements determined by existing bone structure and dentition, whereby the prosthetic components to be fitted onto surgically-placed implant anchors must preferably be designed, shaped and sized specifically to conform to the precise anatomical geometry of the patient, including the location, shape and size of adjoining teeth, and must transition to the precise orientation of the principal axis of the supporting implant anchor with a high degree of accuracy.

In addition, the development of many products and services provided in the fields of orthodontic and restorative dentistry seek to make use of computer aided design (CAD) and computer aided manufacturing (CAM). For example, in dentistry stone or plaster casts made from impressions of the patient's mouth are commonly used to provide the products or services needed, and three dimensional (3-D) scanning of either the patient's dentition or of casts representative of the patient's dentition are used to provide the dental CAD system with data representing the pertinent geometry. For such applications, however, very accurate alignment of the images of the maxilla (or of the upper cast replica) and the mandible (or of the lower cast replica) are needed for dental CAD modeling.

Conventional methods for meeting these rigorous requirements provide for the creation of a model of the patient's jaw and dentition, the making of said model comprising the taking of a so-called "impression" of the patient's dentition, using a malleable substance placed over and around the teeth in the patient's mouth comprising the entire dental arch. Where the placement of implants and restorative components is a factor, typically this impression is taken following the surgical insertion of the implant anchors. Typically, reference components called impression copings are affixed to the external extremity of the inserted implant anchors, and serve to reference the location and angular orientation of the anchors. Subsequently, a model made from a mold based on said impression will incorporate so-called "analog" anchors to model the anchors in the patient's jaw, and prosthetic devices for said anchors will be designed and manufactured based on the geometry of the model created as described.

In actual practice the conventional procedure described above is fraught with numerous difficulties and shortcomings. It has proven impossible for dental practitioners to make dental impressions, and thus models, that are consistently free of dimensional and positional errors; so rigorous are the geometrical requirements involved in such applications that even a sub-millimeter dimensioning error, or a 1 or 2 degree orientation error, will result in prosthetic placements that give rise to unacceptable stresses and conditions.

In recent years efforts have been made to employ image-based modeling techniques to address these well-known problems of conventional implant dentistry procedures. In these efforts, images are taken of the patient's mouth, and a three-dimensional model of the pertinent regions is recreated using so-called three-dimensional image processing techniques and software. The field of photogrammetry, which traces its origins to the decade following the invention of photography in the 1830s, is "the art, science and technology of obtaining reliable information about physical objects and the environment through the processes of recording, measuring, and interpreting photographic images and patterns of electromagnetic radiant energy and other phenomena." (Manual of Photogrammetry, American Society of Photogrammetry and Remote Sensing, 4th Ed., 1980). Particularly with the advent of computers having fast processing speeds and large memories, and the advent of low-cost digital cameras and other image-capture devices, off-the-shelf three-dimensional image processing software has become readily available that is applicable to a wide variety of virtual modeling applications. Using such software, it has become possible to reconstruct reasonably accurate three-dimensional models of an imaged subject field using available commercial products. However the particular demands for great accuracy, and the physical strictures of imaging the human body, have thus far resulted in the absence, in the field of dentistry, of acceptable three-dimensional imaging techniques. A particular problem is the necessity, for the accurate reconstruction, in the form of a virtual model, of an imaged scene. Typically, an object is imaged from more than one position, thereby providing a more complete three-dimensional model.

U.S. Pat. No. 5,851,115 issued Dec. 22, 1998 to Carlsson, et al, describes a photogrammetric method and system for imaging the mouth, for the purpose of creating a virtual model of the patient's mouth from which dental parts may be designed and made. In the system according to Carlsson et al a specialized camera is employed, comprising a set of mirrors that enable a single exposure to embody stereographic images from two different angles. The system of Carlsson further requires that the relative geometry of the virtual "lenses" created by the mirror system be known precisely. To assist the software in locating and orienting imaged features, Carlsson teaches the use of reference markings, such as circles, applied to flat surfaces within the imaged field.

U.S. Pat. No. 5,857,853 issued Jan. 12, 1999 to van Nifteric et al. also discloses a photogrammetry-based method for capturing the dimensional and orientation data required for the manufacture of dental prosthetic parts used in implant dentistry. In order to obtain the at-least-two views required by the triangulation engine of the photogrammetry software, the method of van Nifteric et al employs either a plurality of cameras having precisely-known relative positions, or a single camera mounted on a swiveling carriage that is movable between separated but accurately defined positions. van Nifteric et al. further teach the use of recognition objects and points, to serve as reference points used by the photogrammetry software in positioning features of the imaged scene within a coordinate frame. van Nifteric et al. thus disclose the use of a bar comprising measuring scale markings, and of two spheres mounted on a pin, as recognition objects.

While the methods disclosed in the Carlsson et al. and van Nefteric et al. patents constitute significant advances, these methods still exhibit several important disadvantages and shortcomings that render them impractical for most implant dentistry practitioners. Both of said methods require the use of highly specialized and accordingly expensive camera equipment, and both require that such camera equipment be precisely aligned, to capture a plurality of images from precisely known relative lens positions. Functionally, both methods are inadequate to image accurately a wide field of view, particularly a wide field of view comprising areas characterized by very low feature definition, a condition typical of the edentulous (tooth-free) jaw and thus quite common in implant dentistry practice. The present invention addresses these shortcomings of the prior art, and it provides a three-dimensional-based virtual modeling method, specifically directed to medical and dental applications, that is remarkably low cost and that provides improved feature reconstruction accuracy particularly in applications that require the use of combined three-dimensional images.

Specifically with respect to the problem of providing dental CAD systems with the relative position of maxilla and mandible, prior art methods have depended on two methods that share a common characteristic: the first method relies on capturing the 3-D image of the facial surface of both the maxilla and the mandible in a single image. Separate, individual scans of the maxilla and mandible are then matched to the common template provided by the image of the facial surface of both maxilla and mandible. The second prior art method relies on capturing the "bite registration", or impression of occlusal or biting surfaces of both the upper and lower teeth. After the geometry of the mandible has been captured, the bite registration is placed on the surface of the mandible and it also is scanned. The scan of the maxilla is then matched with the image of the matching surface of the bite registration.

Both of the prior art methods described in the preceding paragraph suffer from two fundamental problems. One problem is computational complexity, and the need to minimize even greater computational complexity by means of a good initial guess by a human operator regarding the relative position of the images being matched. A second and still greater difficulty arises where the patient is partially or completely edentulous, and there is lacking the 3-D information necessary to match the scans of maxilla and mandible. Also, it is difficult to obtain the geometry of anterior teeth from a bit registration.

In some prior art, the object is scanned, using any suitable scanning means capable of capturing a cloud of data points representing three dimensional features of the scanned field. Such scanning typically requires the taking of a plurality of overlapping images that collectively span the image field to cover the required. Various methods are typically employed to recreate the entire three dimensional model from these separate scans. One such prior art method uses precise information about the location of the model with respect to the camera to position and orient the multiple images. In addition, commercially available three-dimensional image processing software products also provide tools to combine discrete scans into a single model by matching the overlapping regions of the images. Well-known examples of suitable image-processing software include the Studio software marketed by Raindrop Geomagic, Inc.

SUMMARY OF INVENTION

Disclosed herein is a three-dimensional-based modeling method and system designed for dentistry and related medical (and appropriate non-medical) applications. One aspect of the method and system dispenses with the need for a specific camera and instead enables the use of any data capture means that produces a point cloud representing the three dimensional surface. Such data capture means may for example be a hand-held or frame-fixed three-dimensional laser scanner, an ordinary digital camera, or any other imaging means that is practically suited to the particular medical application.

Another aspect of the disclosure is the use of three-dimensional recognition objects, to enable the three-dimensional image processing software locate automatically, and determine accurately the position and orientation of objects within the image field.

Yet another aspect of the disclosure is the positioning of recognition objects having well-defined topography within those areas in the image field that have low image definition, and particularly in such of these areas that appear in overlapping portions of at least two images, to provide the three-dimensional image processing software with position, angulation, and orientation information sufficient to enable highly accurate combining (or "stitching") of adjoining and overlapping images.

Still other aspects of the disclosure include methods for accurately capturing the spatial relationship of the maxilla and mandible, said methods not being dependent on the presence of dentition and therefore being fully usable to obtain accurate CAD modeling data even from patients who are partially or wholly edentulous. In the methods disclosed, non-physiological recognition objects or geometry are added to the maxilla and mandible, or to casts representative of the patient's maxilla and mandible, in order to provide precisely accurate geometric references.

In another aspect of the invention, an alternative method for capturing the relative position of the upper and lower components of a dental model makes use of the non-dental planar 3D geometry of these model components. In this alternative method the software registers position determining geometrical features of the model, from 3-D scan data, and employs known characteristics of said geometrical features to locate precisely and accurately all topographical features associated with the models including all anatomical and dental features. Such position determining geometrical features may be a minimum of three intersecting planes on each model component; such features may instead comprise combinations of planes, and/or features such as discs placed or painted on model component planes, spheres, or any other non-dental objects such as will provide unambiguous position data (6 degrees of freedom for each object).

In these methods, recognition objects having a known geometry that comprises well defined features disposed at accurately known or determinable relative positions, are fixedly positioned within the image field, and particularly in areas within the image field that have low feature definition. Examples of recognition objects include one or more spheres having known radii, as well as one or more planar objects of known geometry and dimensions, such as pyramids. The image field is then scanned, such scanning effectively "panning" the image field to cover said image field to provide the needed geometry. Three-dimensional image processing software, preferably comprising algorithms set forth in this specification, is then employed to combine the three-dimensional image data acquired by the scanning means and to determine a virtual three dimensional model that reconstructs, to a high degree of accuracy, the geometry of the scanned image field.

By using physically connected, known geometric features as recognition objects in individual, overlapping or non-overlapping images that collectively cover the field of view of interest, the relative position and orientation of these images can thus be determined. This aspect of the invention serves to eliminate sources of inaccuracy resulting from the known "stitching" methods that result in drift, warp and/or other distortions as scans are aligned.

DETAILED DESCRIPTION

Various aspects of the above-referenced methods and systems will now be presented. In presenting these aspects, embodiments will be used to illustrate features of such methods and systems. It should be understood that these embodiments are shown by way of example only, and are not intended to be limiting in any way. The invention may be embodied both in these and in numerous other forms. While these embodiments illustrate various combinations of elements and acts, it should be appreciated that some or all of such elements or acts may be assembled or practiced in other ways, with or without still further elements or acts, while still practicing the invention.

As used herein, certain terms or expressions should be understood to have the following meanings unless contextual usage clearly indicates otherwise: "Adjacent" the surface of an arch includes placement directly on the arch or spaced slightly therefrom. "Interiorly" and "exteriorly" relate to features toward the interior or exterior, respectively, of a mouth; interiorly or exteriorly with respect to an arch relates to the region within the U-shape of an arch or along the outside of a U-shaped arch, respectively. An edentulous arch is one having no teeth. An arch having an edentulous region has one or more teeth and a portion missing one or more teeth.

An aspect of the present invention is a method and system for creating virtual three-dimensional models of a scanned field of view, using non-physiological objects as reference points in the "stitching" of overlapping captured images, and, additionally, positioning such recognition objects in areas of the field of view that are characterized by low feature definition in order to enhance the accuracy of the three-dimensional modeling of such areas.

A further aspect of the present invention is a method and system for obtaining 3-D data, usable in CAD and CAM applications, concerning the relative position of individual components such as the mandible and maxilla of a dental patient, especially when the 3-D data from each component must be scanned separately.

The described systems and methods are particularly suitable and intended for medical and dental applications, and are particularly suited for use in the field of implant dentistry and related applications. Dental implants are used to support the restoration of missing teeth. Implant fixtures are surgically implanted by a dentist. These dental implants typically will be "restored" with abutments and crowns; that is, following successful implantation of implant fixtures into the jaw of the patient, complementary components including abutments and crowns will be affixed to the implanted fixtures to provide the patient with a restoration of the patient's natural teeth.

In an aspect, a method and system in accordance with some embodiments of the present invention enables a manufacturer of dental restoration components to accurately measure the location and orientation of the implants in relation to the surrounding oral environment, and thereby to design and to machine restoration components that are, to a very high degree of precision and accuracy, customized to the anatomy and the existing dentition of the patient.

In applications directed to dentistry, and related medical applications, such methods and systems dispense with the need for specialized camera(s) and camera mountings. Instead they enable the use of any data capture means that produces a point cloud representing the three dimensional surface. Such data capture means may for example, be a hand-held or frame-fixed three-dimensional laser scanner, an ordinary digital camera, or any other imaging means that is practically suited to the particular medical application. Image-data capturing means usable with the invention are readily available from commercial sources, and would for example include three-dimensional laser scanners, such as the VIVID 900 model scanner marketed by the Minolta Corporation.

Figure 8:
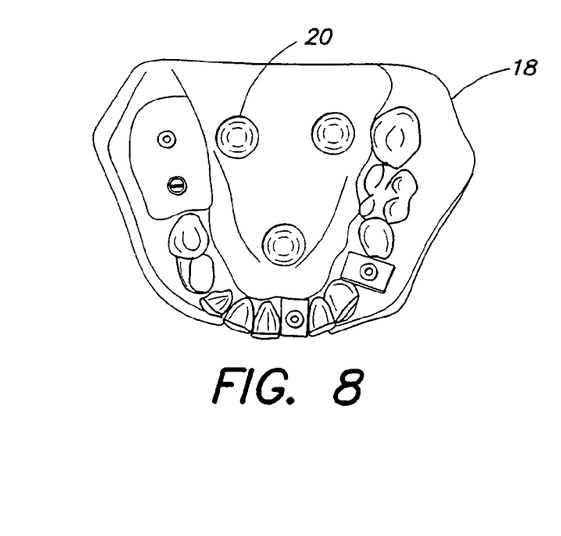
FIG. 8 is a view of a cast of maxilla showing impressions made by the three recognition objects of the FIG. 7 cast.

Another aspect of the invention is the use of recognition objects, such as illustrated in FIGS. 1-6 and in FIG. 8, to assist three-dimensional image processing software to locate automatically, and to determine accurately the position and orientation of objects within the image field.

A still further aspect of the invention is the positioning of recognition objects having well-defined topography within those areas in the image field that have low image definition, and particularly in such of these areas that appear in overlapping portions of at least two images, to provide the imaging software with position and orientation information sufficient to enable highly accurate combining (or "stitching") of adjoining and overlapping images. The presence of such areas of low feature definition is typical of edentulous dental conditions, and thus presents a chronic problem to the imaging of edentulous jaws, which the present invention is the first to address successfully.

Figure 1:
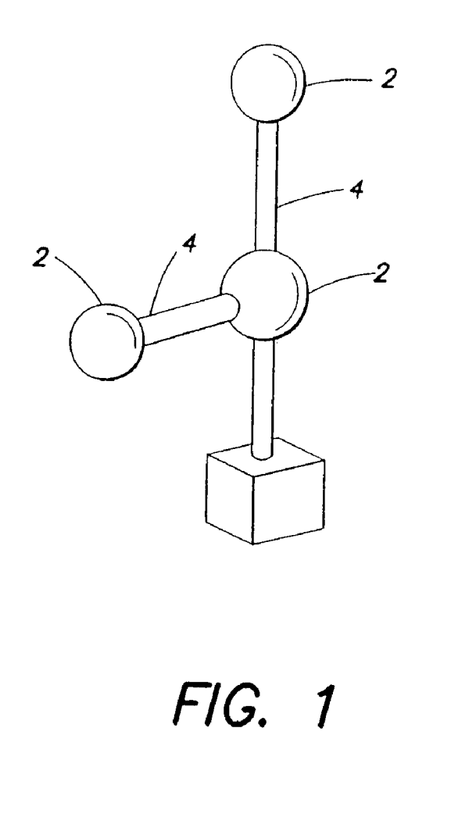
FIG. 1 is a perspective view of a first recognition object usable according to the disclosed methods and system.
Figure 2:
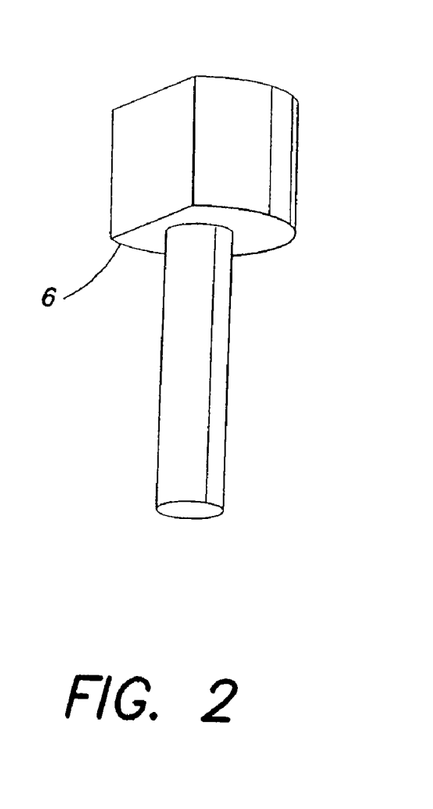
FIG. 2 is a perspective view of a second recognition object usable according to the disclosed methods and system.
Figure 3:
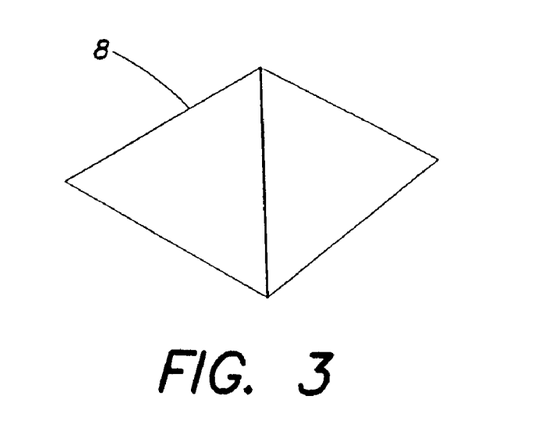
FIG. 3 is a perspective view of a third recognition object usable according to the disclosed methods and system.

In practicing the approach taught herein, recognition objects having a known geometry that comprises well defined features disposed at accurately known or determinable relative positions, are fixedly incorporated within the image field, and particularly in areas within the image field that have low feature definition. Some embodiments of recognition objects for use with this technology include an object, such as illustrated in FIG. 1, that comprises three linked spheres 2 having precisely known radii, fixed at precisely known positions on angled posts 4 or an object comprising a three-dimensional shape 6, such as illustrated in FIG. 2. Another useful form of recognition object is the use of multiple planes as shown in FIG. 3 an example being a pyramidal polygon 8 of known dimensions. Still another useful form of recognition object is a simple sphere of known radius, as illustrated for example in FIGS. 5-7 and 9 (see, e.g., spheres 36 in arch 38 of FIG. 5).

In the practice of the method taught herein, recognition objects as shown in FIGS. 1-4 are incorporated within the image field. In the case of implant dentistry, one or more recognition objects can be secured to dental implants that have been surgically implanted into the jaw of the patient. Preferably, such recognition objects each comprise an attachment feature that is complementary to the interface features of the dental implant. The recognition objects can be secured with a fastener having a threaded shaft insertable within a bore of the recognition object that may be oriented along the principal axis of the implant fixture. Where the field of view comprises articulated casts of the maxilla and mandible of a patient, the recognition objects may be secured to posts screwed into or otherwise secured to the casts.

According to another aspect, the invention comprises a method and system for developing a virtual three-dimensional model of a dental restoration field. In one aspect, the invention provides means for determining the relative location of recognition objects, and of features of recognition objects, in one or a plurality of scanned images obtained with a three-dimensional scanning means, and for detecting the location and the orientation of a known feature in a three-dimensional scanned object.

In another aspect, the invention comprises a system and methods for accurately capturing the spatial relationship between two separate bodies, such as the maxilla and mandible of a dental patient, utilizing recognition objects positioned upon or secured to the bodies (i.e., to the maxilla and mandible or to casts or impressions representative of the maxilla and mandible).

The recognition object can be an intrinsic, but non-anatomic, feature of an original object (or set of objects) as well as being an artifact that is added to the original object field. In either case the recognition object has known geometry. Using information about the known geometry of the recognition object, software enables the precise position and orientation of the recognition object to be identified with respect to the scanned data. Furthermore, multiple scans of a given field of view can be "registered" and their relative position and/or orientation precisely aligned, without any human intervention. Similarly the relative position and orientation of two or more objects, notably including fields of view consisting of two separately scanned components, such as maxilla and mandible, or their representative casts, may be accurately aligned with precision and a high degree of dimensional accuracy, using multiple scans of each field of view and at least one scan encompassing recognition objects from each of said fields of view.

A field of view to be scanned must therefore comprise at least one object having one or more recognition features of known geometry and dimension, said features being sufficient to completely define location and/or orientation. Non-limiting examples of these types of objects are shown in FIGS. 1-7. The recognition (location) object is scanned using a three-dimensional scanner, and the scanned data is often collected as unordered ASCII text format; however any collection of three-dimensional point data is applicable.

From the scanned data the recognition object(s) are detected by the imaging software, and the determination of the position and/or orientation of each (using its known geometry) enables also the determination of the position and orientation of all other objects and features captured in the scanned data.

This process can be rapidly executed in a fully automated process employing efficient computer code. For example, in the example of three spheres used to define position and orientation (see FIG. 1), the centers of the three spheres (of known diameter and known distance from each other) are detected by the software. An origin is then calculated using the geometric relationship, and the location of the origin is typically output as a data point triple (x,y,z). The software may also calculate the orientation of the recognition object as two unit vectors, also expressed as data point triples. Similar methods are employed to determine the position and orientation defined by other objects of known geometry within the subject field, such as the spherical, planar, polygonal, cylindrical and other shapes shown in FIGS. 1-7. In this way a set of data is obtained that fully defines the position and orientation of each recognition object.

Detecting an object of known geometry in a 3-dimensional scan has many potential applications. The medical and dental applications to which the present invention is principally directed involve a combination of organic surfaces and manufactured objects, and, in these applications, the ability to detect, to a high degree of accuracy, the position and orientation of an object of known geometry which is positioned within an anatomical field of view occasions the ability to design component parts that are customized to the topography of this anatomical field of view.

Specifically in the case of dental implants, for example, by mounting one of the recognition objects shown in FIGS. 1-3 onto the existing manufactured part (i.e., the implant itself), the exact location and orientation of this part within the dental arch of the patient can be determined relative to other recognition objects. In turn, this determination permits a virtual assembly to be made that combines the scanned image and proposed replacement and supplemental part (i.e. a replacement tooth), in order to select, and then manufacture, replacement and supplemental parts that exactly complement the geometrical requirements of the patient's anatomical conditions. Furthermore, the placement of recognition objection within an edentulous region, or other region without significant anatomical features, enables accurate registration of scans that contain the recognition object.

When multiple three-dimensional images of an object are taken (e.g. due to size or obscured views), it is necessary to define the relative location and orientation of each of the images in order to re-align the captured image data into a complete and accurate representation of the original field of view. In order to do this, there must be captured, in each image in the set of images, a recognition object of known geometry (such as those shown in FIGS. 1-7), which also appears in a second image in the set. The location and/or orientation of the known object in each image can then be used to position the images with respect to each other in order to recreate the original field of view.

This method can also be employed in conjunction with and to supplement currently practiced "stitching" or "registration" methods. These methods align multiple scans without the use of known geometry, but are insufficiently accurate for many applications. The addition to the field of view of one or more recognition objects according to the invention, as illustrated for example in FIGS. 1-6, greatly enhances the accuracy of the stitching of adjoining images. Furthermore the positioning of such recognition objects within any areas of the field of view that are characterized by low feature definition will greatly enhance the three-dimensional modeling of such areas, in addition to serving as relative reference points between adjoining images that each comprise a given recognition object.

In particular, the described methodology enables the precise co-relation and registration of separate digitized scans of the maxilla and mandible of a dental patient (or of scans of casts representing, respectively, the maxilla and mandible of a patient). Three dimensional models developed from these methods enable an accurate definition of the positions and orientations of the maxilla and mandible, including a precise determination of the topographical aspects which determine occlusion characteristics. Such 3-D models may then be used to develop dental restorations that properly account for the optimal location/orientation of occlusal contacts and surfaces.

Figure 6:
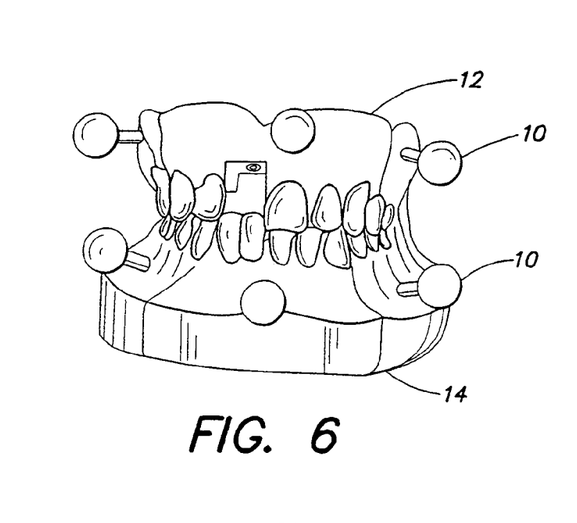
FIG. 6 is a perspective view of recognition objects placed externally to casts representing a patient's maxilla and mandible.
Figure 7:
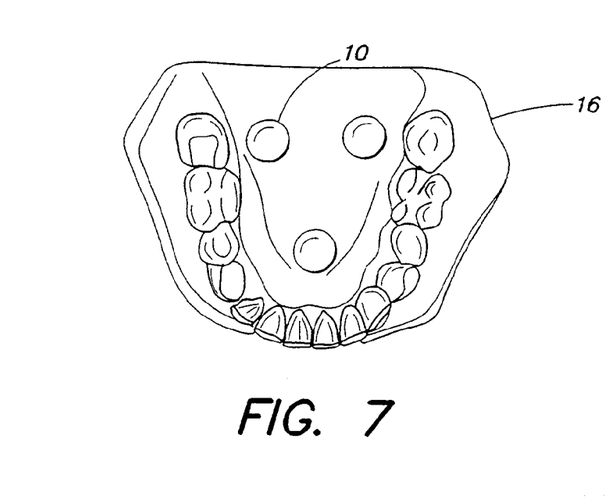
FIG. 7 is a view of a cast of mandible comprising three internally placed recognition objects.

A first method for effecting an accurate registration of the relative position of maxilla and mandible utilizes the recognition components illustrated in FIG. 6. As shown in FIG. 6, a set of three spheres 10 of known radii are affixed externally to, respectively, a cast of the patient's maxilla 12 and a cast of the patient's mandible 14. Following separately-effected digitized scans of maxilla and mandible, a scan or set of scans that captures all of the spheres thus positioned on maxilla and mandible as shown on FIG. 6 can be used to construct a three-dimensional model that accurately represents the respective positions, orientations, and dimensions of the mandible and maxilla and their respective features.

Figure 9:
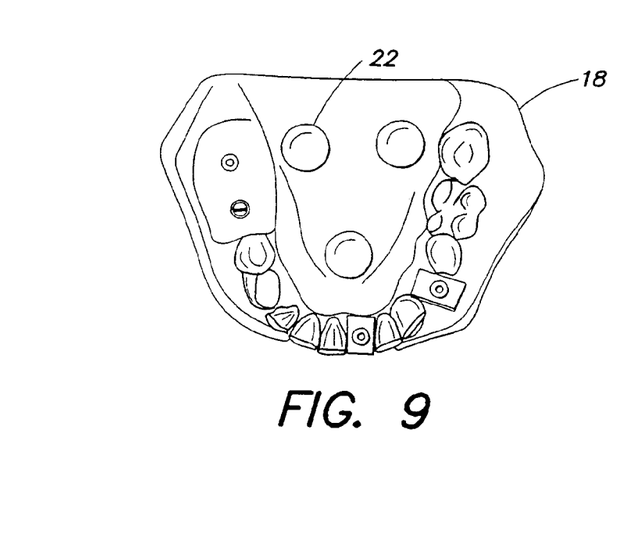
FIG. 9 is a view of the cast shown in FIG. 8, now comprising spheres placed in impressions visible in FIG. 8

In a second method according to the invention, for developing a 3-D model of the articulated relation between the maxilla and mandible of a patient, only a single set of (preferably) three spheres is used. The set of spheres is positioned within the maxillar or mandibular arch of a patient, or, as in FIG. 7, a cast 16 representing such an arch is made, and an "impression" is taken of the impact of that set of objects upon a pliable material placed within the opposing jaw element. Scans are then taken of the respective jaws 18, either with the "impacted" surface left as is (as shown in FIG. 8) for imaging of the indentations 20 created by the recognition objects, or, for better illumination, following the placement of additional, identically-sized reflective spheres 22 within the indentations (FIG. 9).

Figure 4:
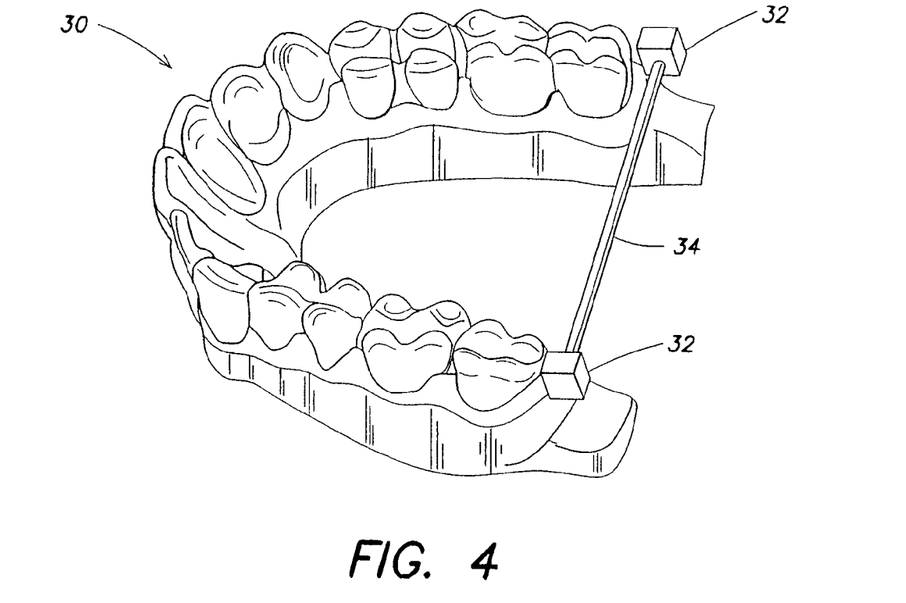
FIG. 4 is a perspective view of a dental arch comprising a third recognition object.
Figure 5:
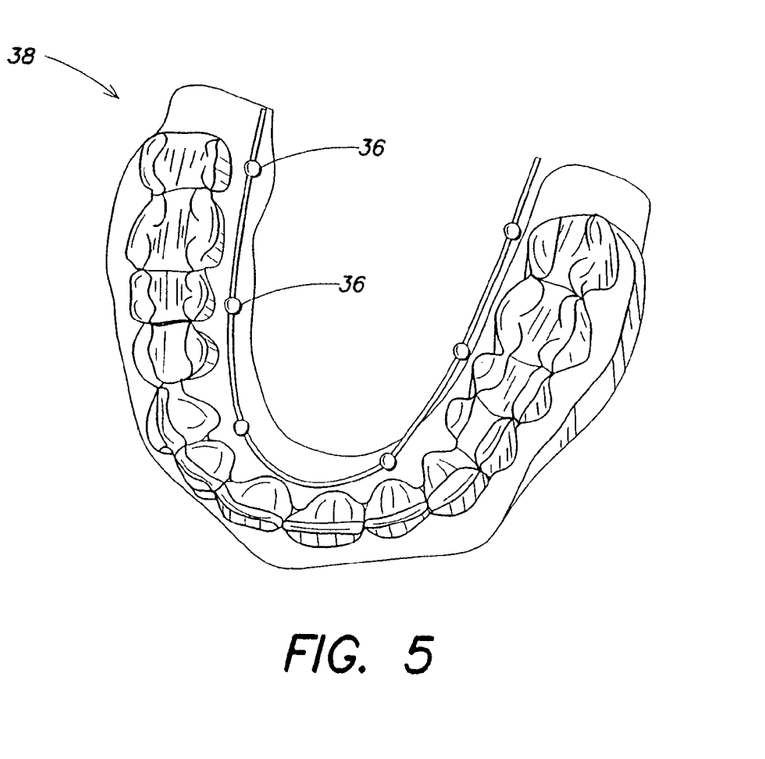
FIG. 5 is a perspective view of a dental arch comprising a fourth recognition object.

By using physically connected, known geometric features as recognition objects in individual, overlapping or non-overlapping images that collectively cover the field of view of interest, the relative position and orientation of these images can thus be determined. This aspect of the invention serves to eliminate sources of inaccuracy resulting from the known "stitching" methods that result in drift, warp and/or other distortions as scans are aligned. FIG. 4 illustrates an example of this solution: in this case, a dental arch 30 is to be scanned. The known geometry introduced into the scan, in the form of two polygons 32 of known dimensions, linked by a bar 34 also having a known dimension, enables detection of location and/or orientation of scans of portions of the teeth. Intra-oral scanning necessitates the use of small scanners, such that each scan enables the capture of only a portion of the arch.

In the practice of the invention, spatial information may be obtained directly using intra-oral scanning and then processed as described above. As described above, however, the present invention may be used in conjunction with the conventional practice whereby impressions are taken of the patient's dentition, and said dentition is replicated in the form of a master cast made from said impressions. In an implant case, the master cast will contain analogs of the dental implants. The accuracy with which the locations and orientations of these implant analogs can be determined, for the purpose of designing restoration component parts to be supported by the implants, is enhanced by using a recognition object according to the present invention.

In another aspect of the invention, an alternative method for capturing the relative position of the upper and lower components of a dental model, and thereby for "aligning" said model components, makes use of the non-dental planar 3D geometry of these model components. In this alternative method the software registers position determining geometrical features of the model, from scan data, and employs known characteristics of said geometrical features to locate precisely and accurately all topographical features associated with the models including all anatomical and dental features. Such position determining geometrical features may be a minimum of three intersecting planes on each model component; such features may instead comprise combinations of planes, and/or features such as discs placed or painted on model component planes, spheres, or any other non-dental objects such as will provide unambiguous position data (6 degrees of freedom for each object).

Figure 10:
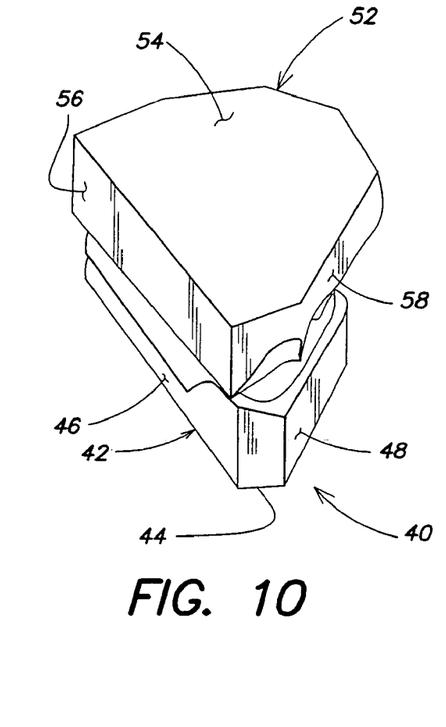
FIG. 10 is a perspective view of an assembled dental model, showing characteristic planar surfaces.
Figure 11:
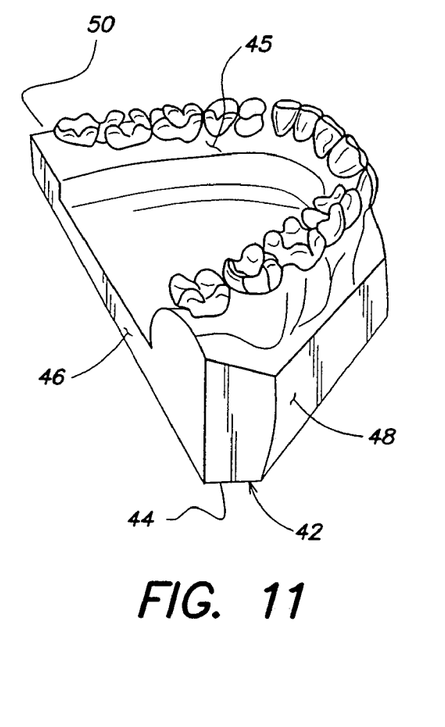
FIG. 11 is a perspective view of the lower component of the dental model of FIG. 10.
Figure 12:
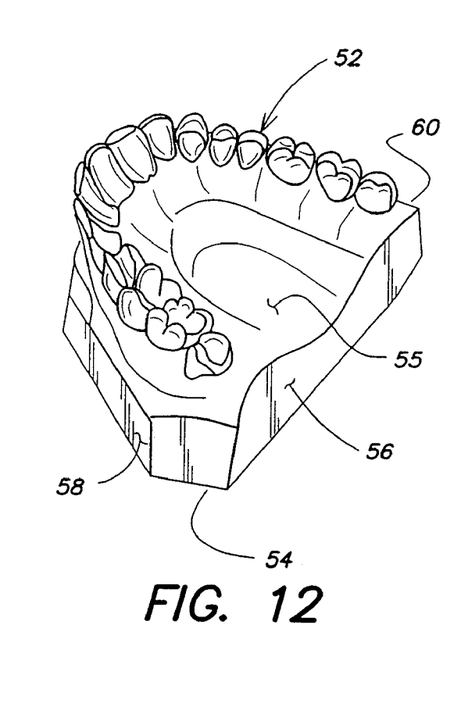
FIG. 12 is a perspective view of the upper component of the dental model of FIG. 10.

Referring to FIGS. 10, 11, and 12, a typical dental model is illustrated, comprising a lower component (shown separately in FIG. 11) and an upper component (shown separately in FIG. 12). As shown in FIGS. 10-12, dental models generally have multiple plane surfaces as a result of their preparation (or such planes can readily be added), and these planes provide a rich source of position-determining data, which can be extracted from scans of the model to serve as the basis for locating the positions of all topographical features associated with the model.

Referring to FIG. 11, there is illustrated lower component 42 of model 40. Lower component 42 comprises a plurality of planar surfaces, as artifacts of the preparation of the model, or created subsequently to the preparation of the model and specifically to serve as position-determining reference features. Said planar surfaces include a bottom plane 44 (not visible in FIG. 11, but opposite lower dental arch 45), a back plane 46, a first (e.g., right) side plane 48 and a second (e.g., left) side plane 50. Similarly, upper model component 52, shown separately in FIG. 12, comprises a bottom plane 54 (not visible in FIG. 12, but opposite upper dental arch 55), a back plane 56, a first plane 58, and a second plane 60. In particular, the planar surface forming the "bottom" of each model component can be used as a reference feature (the "bottom" of a model component being the planar surface opposite the dental arch surface of the component). In the following example, bottom plane 44 of lower model component 42 (shown separately in FIG. 11) is used as a reference plane; however, another planar surface of the either model component may be used instead as a reference. Similarly, three planes were chosen for this example, but three or more planes or a combination of planes and other non-dental features could also have been chosen. (In some instances, one or more dental features can even be used as recognition features, augmented by planar and/or other non-dental features.)

Alignment of the lower model component with the upper model component is implemented in this example by the use of three planes from each model component. It should be noted that, in the particular images of these respective model components employed to effect the alignment, the selected planes from the upper and lower models do not have to be aligned in any particular manner, in order to develop an accurate alignment of the upper and lower model components. (If non-planar features exist on or near the planes of interest, these can and generally should be removed using suitable processing techniques known in the art.)

The assembled model (FIG. 10) provides the relative location of the planes required for the assembly of the individual 3-D images respectively of the lower model component (FIG. 11) and of the upper model component (FIG. 12). Three planes from each model are selected. As the assembled model is illustrated in FIG. 10, and as lower model component 42 is illustrated in FIG. 11, bottom plane 44 of lower model 42 is not visible; likewise, in FIGS. 12, bottom plane 54 of upper model component 52 is not visible. However, the bottom plane of each model component rests on the reference plane of the 3-D scanner at the time of scanning, preferably aligned with one or more reference markings, and therefore the geometrical orientation of these bottom planes in the scans is known.

Since the bottom plane in each of the three images (assembled, lower, and upper) is known, then, for each of the upper and lower components, only two additional planes, each visible in both the separate image of the component and the image of the assembly, need to be determined by the software in order to determine precisely the geometry of that component. Similarly, for determining the geometry, and thus the alignment of upper and lower components, of the fully assembled model, there must be determined, from its image as represented in FIG. 10, the two planes selected from each of the model components plus only the previously invisible, but "known", bottom plane 54 of upper model component 52.

For example, the geometry of lower model component 42 may be determined from knowledge of the plane of its bottom 44 (invisible in FIG. 11) and determination of lower component back plane 46 and lower component side plane 48. Similarly the geometry of upper model component 52 may be determined from knowledge of the plane of its bottom 54 (invisible in FIG. 12) and determination of upper component back plane 56 upper lower component side plane 58. Given the locations of the above planes the individual images can be assembled to match the locations of the planes in the assembly.

Thus, to implement the alignment of the upper and lower model components of model 40, from the image of the assembled model shown in FIG. 10, it is necessary only to determine the orientation, in this image, of the four planes (two from each model component) described above (that is, upper component back plane 46 and side plane 48, and lower component back 56 and side plane 58), and additionally, to determine the orientation, as shown in FIG. 10, of upper component bottom plane 54.

More than three planes can also be used, as well as other objects that over-constrain the solution to the position of the model components (though if over-constrained a least squares, or similar solution, may typically be preferred). Optionally, additional reference features may be attached to the planar surfaces of model component surfaces, also to serve as position-determining reference features. For example, small circular disks of a color contrasting with that of the model surfaces, may be painted on or otherwise adhered to any surface. Two or more such disks may also be disposed on the same planar surface at precisely measured spaced apart positions, thereby providing a scalar measure.

What is claimed is:

1. A method for constructing a 3-D model incorporating 3-D scan image data of a maxillar dental arch and of an opposing mandibular dental arch, said method comprising:
   disposing a number of recognition features adjacent the surfaces of each of the maxillar and mandibular dental arches, the recognition features permitting determination of the respective positions and orientations of said dental arches;
   individually 3-dimensionally scanning said dental arches to obtain 3-D image data including data representing topographical features of said dental arches and the recognition features associated with each of said dental arches;
   3-dimensionally scanning said dental arches while said dental arches are in an occlusal relationship to obtain 3-D image data including data representing the recognition features associated with each of said dental arches;
   processing said 3-D image data; and
   constructing a 3-D model including a maxillar dental arch representation aligned with a mandibular dental arch representation.

2. The method of claim 1 wherein said dental arches are formed in impressions or casts of a patient's maxillar and mandibular dental arches.

3. The method of claim 1 wherein at least one recognition feature is placed exteriorly to at least one of said dental arches.

4. The method of claim 1 wherein at least one recognition feature is placed interiorly to at least one of said dental arches.

5. The method of claim 1 wherein at least one of said dental arches is edentulous.

6. The method of claim 1 wherein neither arch is edentulous.

7. The method of claim 6 wherein at least one of said dental arches has an edentulous region.

8. The method of claim 1, wherein at least one of said maxillar dental arch and said mandibular dental arch includes a portion associated with a dental implant, wherein said disposing includes disposing at least one of the recognition features in a fixed location and orientation relative to the portion of said at least one dental arch associated with the dental implant, said at least one recognition feature permitting determination of the location and orientation of the dental implant, and wherein said 3-D model includes a portion representing the location and orientation of the dental implant.

9. A method for constructing a 3-D model incorporating 3-D scan image data of a maxillar dental arch and an opposing mandibular dental arch, at least one of said maxillar dental arch and said mandibular dental arch including a portion associated with a dental implant, said method comprising:
   disposing at least one recognition feature adjacent the surface of said at least one of the maxillar dental arch and the mandibular dental arch, said at least one recognition feature being disposed in a fixed location and orientation relative to the portion of said at least one dental arch associated with the dental implant, said at least one recognition feature permitting determination of the location and orientation of the dental implant;
   3-dimensionally scanning said maxillar dental arch and said mandibular dental arch, wherein said 3-dimensionally scanning includes 3-dimensionally scanning said maxillar dental arch and said mandibular dental arch while said arches are in an occlusal relationship, and wherein said 3-dimensionally scanning obtains 3-D image data including data representing topographical features of said at least one dental arch and said at least one recognition feature;

processing said 3-D image data; and constructing a 3-D model including a maxillar dental arch representation aligned with a mandibular dental arch representation, said 3-D model further including a portion representing the location and orientation of the dental implant.

10. The method of claim 9, wherein said dental arches are formed in impressions or casts of a patient's maxillar and mandibular dental arches.

11. The method of claim 9, wherein said at least one dental arch includes a cast of at least one of a patient's maxillar dental arch and a patient's mandibular dental arch, and wherein said disposing includes attaching said at least one recognition feature to a post secured to the cast.

12. The method of claim 9, wherein said disposing includes attaching said at least one recognition feature to a dental implant implanted in a jaw of a patient.

13. The method of claim 9, wherein said disposing further includes associating an attachment feature of said at least one recognition feature with an interface feature of said implanted dental implant, said attachment feature being complementary to said interface feature.

14. The method of claim 9, wherein said disposing further includes attaching said at least one recognition feature to said implanted dental implant via a fastener having a threaded shaft.

15. The method of claim 9, wherein said disposing further includes orienting said at least one recognition feature along a principal axis of the implanted dental implant.

16. The method of claim 9, wherein said at least one dental arch is edentulous.

17. The method of claim 9, wherein said portion of said dental arch includes an edentulous region.

18. The method of claim 9, further comprising disposing a plurality of additional recognition features adjacent the surfaces of each of the maxillar and mandibular dental arches, the additional recognition features permitting determination of the respective positions and orientations of said dental arches, wherein said 3-D image data obtained in said 3-dimensionally scanning includes data representing said plurality of additional recognition features.

19. The method of claim 9, wherein said 3-dimensionally scanning further includes individually 3-dimensionally scanning said maxillar dental arch and said mandibular dental arch.

* * * * *